US009919344B2

(12) United States Patent
Schafer

(10) Patent No.: US 9,919,344 B2
(45) Date of Patent: Mar. 20, 2018

(54) FLEXTENSIONAL TRANSDUCERS AND RELATED METHODS

(71) Applicant: Photosonix Medical, Inc., Ambler, PA (US)

(72) Inventor: Mark E. Schafer, Ambler, PA (US)

(73) Assignee: PHOTOSONIX MEDICAL, INC., Ambler, PA (US)

(*) Notice: Subject to any disclaimer, the term of this patent is extended or adjusted under 35 U.S.C. 154(b) by 255 days.

(21) Appl. No.: 14/585,508

(22) Filed: Dec. 30, 2014

(65) Prior Publication Data

US 2015/0187349 A1 Jul. 2, 2015

Related U.S. Application Data

(60) Provisional application No. 61/921,735, filed on Dec. 30, 2013.

(51) Int. Cl.
*G01K 11/18* (2006.01)
*B06B 1/06* (2006.01)
(Continued)

(52) U.S. Cl.
CPC ............ *B06B 1/0644* (2013.01); *G10K 9/121* (2013.01); *H04R 17/005* (2013.01)

(58) Field of Classification Search
CPC .......... B06B 1/06; G10K 11/18; G10K 9/121; H04R 17/00
See application file for complete search history.

(56) References Cited

U.S. PATENT DOCUMENTS

| | | | | | |
|---|---|---|---|---|---|
| 2,403,692 | A * | 7/1946 | Tibbetts | G10K 9/122 | 29/25.35 |
| 2,487,962 | A * | 11/1949 | Arndt, Jr. | H04R 17/00 | 310/328 |

(Continued)

FOREIGN PATENT DOCUMENTS

| | | | |
|---|---|---|---|
| WO | 9309641 | A1 | 5/1993 |
| WO | 2008061493 | A1 | 5/2008 |

OTHER PUBLICATIONS

The International Bureau of WIPO, International Preliminary Report on Patentability issued in International Application No. PCT/US2014/072719 dated Jul. 5, 2016.

(Continued)

*Primary Examiner* — Luke D Ratcliffe
*Assistant Examiner* — Amie M Ndure
(74) *Attorney, Agent, or Firm* — Thompson Hine LLP

(57) ABSTRACT

Flextensional transducers and methods of using flextensional transducers. The transducer includes a piezoelectric element and may include at least one endcap coupled with the piezoelectric element. The endcap may have an outer portion formed of a first material and an inner portion formed of a second material having a greater flexibility than the first material. The endcap may be coupled with an annular piezoelectric element near either its outer circumference or its inner circumference. The piezoelectric element may be a planar disk or have a curved bowl-shape. The transducer may be coupled with, and at least partially restrained by, a support structure. The transducer may also be configured to permit light to pass therethrough.

25 Claims, 9 Drawing Sheets

(51) Int. Cl.
*G10K 9/12* (2006.01)
*H04R 17/00* (2006.01)

(56) References Cited

U.S. PATENT DOCUMENTS

| | | | | |
|---|---|---|---|---|
| 2,895,062 | A | 7/1959 | Abbott | |
| 4,845,688 | A | 7/1989 | Butler | |
| 4,999,819 | A | 3/1991 | Newnham et al. | |
| 5,276,657 | A | 1/1994 | Newnham et al. | |
| 5,729,077 | A * | 3/1998 | Newnham | H02N 2/043 310/328 |
| 6,232,702 | B1 * | 5/2001 | Newnham | G10K 9/121 310/324 |
| 6,398,753 | B2 | 6/2002 | McDaniel | |
| 6,407,484 | B1 | 6/2002 | Oliver et al. | |
| 6,438,242 | B1 | 8/2002 | Howarth | |
| 6,465,936 | B1 * | 10/2002 | Knowles | H02N 2/043 310/328 |
| 6,533,803 | B2 | 3/2003 | Babaev | |
| 6,554,761 | B1 * | 4/2003 | Puria | H04R 25/606 381/114 |
| 6,614,143 | B2 * | 9/2003 | Zhang | G10K 9/121 310/317 |
| 6,629,922 | B1 * | 10/2003 | Puria | H04R 25/606 381/312 |
| 6,965,189 | B2 * | 11/2005 | Menzel | H01L 41/107 310/328 |
| 7,379,392 | B1 | 5/2008 | Benjamin | |
| 7,474,495 | B2 * | 1/2009 | Weng | G11B 5/5504 360/101 |
| 8,206,326 | B2 | 6/2012 | Schafer et al. | |
| 8,523,791 | B2 | 9/2013 | Caster | |
| 8,574,174 | B2 | 11/2013 | Schafer et al. | |
| 8,659,209 | B2 * | 2/2014 | Rahman | E21B 23/00 310/328 |
| 9,061,128 | B2 | 6/2015 | Hall et al. | |
| 2003/0032900 | A1 | 2/2003 | Ella | |
| 2004/0242956 | A1 * | 12/2004 | Scorvo | A61F 2/0022 600/30 |
| 2010/0052480 | A1 * | 3/2010 | Wagner | H02N 2/043 310/348 |
| 2011/0184499 | A1 | 7/2011 | Radi | |
| 2012/0029394 | A1 | 2/2012 | Babaev | |
| 2012/0119620 | A1 | 5/2012 | Xu et al. | |
| 2012/0209151 | A1 | 8/2012 | Zhou et al. | |
| 2014/0276247 | A1 | 9/2014 | Hall et al. | |
| 2015/0100002 | A1 | 4/2015 | Choi | |

OTHER PUBLICATIONS

Patent Cooperation Treaty, PCT/US2014/072719, Invitation to Pay Additional Fees and, Where Applicable, Fees and Partial International Search Results, dated May 8, 2015 (7pages).
Xu et al. "Piezoelectric composites with high sensitivity and high capacitance for use at high pressures." IEEE Transactions on Ultrasonics, Ferroelectrics, and Frequency Control. vol. 38, No. 6, Nov. 1991, 634-639.
Rolt. "History of the flextensional electroacoustic transducer." J. Acoust. Soc. Am. 87(3), Mar. 1990, 1340-49.
Zhang et al. "A class V flextensional transducer: the cymbal." Ultrasonics. 37 (1999) 387-93.
Dogan et al. "Composite piezoelectric transducer with truncated conical endcaps "cymbal"." IEEE Transactions on Ultrasonics, Ferroelectrics, and Frequency Control. vol. 44, No. 3, May 1997, 597-605.
Butler et al. "A low frequency directional flextensional transducer and line array." J. Acoust. Soc. Am. 102(1), Jul. 1997, 308-314.
Xu et al. Ceramic-Metal Composite Actuator. 1991 IEEE Ultrasonics Symposium, 923.

* cited by examiner

FLEXTENSIONAL TRANSDUCERS AND RELATED METHODS

CROSS-REFERENCE TO RELATED APPLICATIONS

This application claims the benefit of U.S. Provisional Application Ser. No. 61/921,735, filed Dec. 30, 2013 the disclosure of which is hereby incorporated by reference herein in its entirety.

BACKGROUND

The present invention relates generally to electro-acoustic transducers and, more particularly, to flextensional transducers and methods of using flextensional transducers.

Flextensional transducers are known for their traditional use as high-power, low-frequency ultrasound sources in underwater acoustic applications. Among other end uses, they have been adapted for use as low-power, low-frequency transducers for medical ultrasonic applications. Flextensional transducers currently used in such medical ultrasonic applications generally include a solid piezoelectric ceramic disk arranged between a pair of metal endcaps. When the ceramic disk is energized with a current of alternating polarity, the ceramic disk expands and contracts radially in a sinusoidal manner. This radial expansion and contraction is mechanically transferred to the endcaps, causing the endcaps to flex outwardly or inwardly so as to amplify the mechanical motion generated by the ceramic disk. In turn, the rapid sinusoidal flexing of the endcaps generates ultrasonic sound waves that are emitted outwardly from each of the endcaps.

Flextensional transducers are structurally symmetric in both axial and radial directions of the ceramic disk, and thus radiate sound waves equally in two opposed directions, outwardly from each endcap. This results in waste of sound energy in applications where radiation is required to be emitted in only one direction. Furthermore, such transducers have been encapsulated in epoxy or polymers in order to create arrays of elements to increase the total area for radiation of sound energy. Such encapsulated transducers are "floating" within the encapsulation and not mounted or otherwise secured to a support structure. This mounting arrangement may result in excessive vibration of, and stress on, conductive wiring connected to the transducer.

Improved flextensional transducers and methods of using flextensional transducers are needed.

SUMMARY

An exemplary embodiment of a flextensional transducer includes a piezoelectric element and at least one endcap coupled with the piezoelectric element. The endcap has an outer portion formed of a first material and an inner portion formed of a second material different from the first material. The flextensional transducer may be operable to emit sound energy.

Another exemplary embodiment of a flextensional transducer includes a piezoelectric element, as well as a first endcap and a second endcap that are each coupled with the piezoelectric element. The first endcap has a first maximum outer diameter, and the second endcap has a second maximum outer diameter that is less than the first maximum outer diameter. The flextensional transducer may be operable to emit sound energy.

Another exemplary embodiment of a flextensional transducer includes a piezoelectric element, and a first endcap coupled with the piezoelectric element. A portion of the flextensional transducer is coupled with a support structure and is at least partially restrained against movement relative to the support structure. The flextensional transducer may be operable to emit sound energy.

Yet another exemplary embodiment of a flextensional transducer includes a curved piezoelectric element, and an endcap coupled with the curved piezoelectric element. The flextensional transducer may be operable to emit sound energy.

In an exemplary embodiment, a method of emitting sound energy with a flextensional transducer includes energizing a piezoelectric element with an alternating current signal so that the piezoelectric element generates mechanical energy and transferring the mechanical energy from the piezoelectric element to at least one endcap coupled with the piezoelectric element. In response to the mechanical energy transfer, an inner portion of the at least one endcap is allowed to flex with a greater displacement in an axial direction than an outer portion of the at least one endcap. The sound energy is emitted from the at least one endcap as a result of the flexing of the at least one endcap.

In another exemplary embodiment, a method of emitting sound energy with a flextensional transducer includes energizing an annular piezoelectric element with an alternating current signal so that the annular piezoelectric element generates mechanical energy, transferring a portion of the mechanical energy from the annular piezoelectric element to a first endcap coupled therewith at a location proximate an outer circumference of the annular piezoelectric element, and transferring a portion of the mechanical energy from the annular piezoelectric element to a second endcap coupled therewith at a location proximate an inner circumference of the annular piezoelectric element. In response to the transferred mechanical energy, the first endcap and the second endcap are allowed to flex relative to the piezoelectric element. The sound energy is emitted from the first endcap and the second endcap as a result of the flexing of the first and second endcaps.

In another exemplary embodiment, a method of emitting sound energy with a flextensional transducer coupled with a support structure includes energizing a piezoelectric element with an alternating current signal so that the piezoelectric element generates mechanical energy, and transferring the mechanical energy from the piezoelectric element to an endcap coupled with the piezoelectric element. In response to the transferred mechanical energy, the endcap is allowed to flex relative to the piezoelectric element. The sound energy is emitted from the endcap as a result of the flexing of the endcap while at least partially restraining movement of a portion of the flextensional transducer relative to the support structure.

In yet another exemplary embodiment of a method of emitting sound energy with a flextensional transducer includes energizing a curved piezoelectric element with an alternating current signal so that the curved piezoelectric element expands and contracts in a direction relative to a focal point defined by the curvature of the curved piezoelectric element to generate mechanical energy, and transferring the mechanical energy from the curved piezoelectric element to an endcap coupled with the curved piezoelectric element. In response to the transferred mechanical energy, the endcap is allowed to flex relative to the curved piezoelectric element, and the sound energy is emitted from the endcap as a result of the flexing of the endcap.

BRIEF DESCRIPTION OF THE SEVERAL VIEWS OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION

Figure 1:
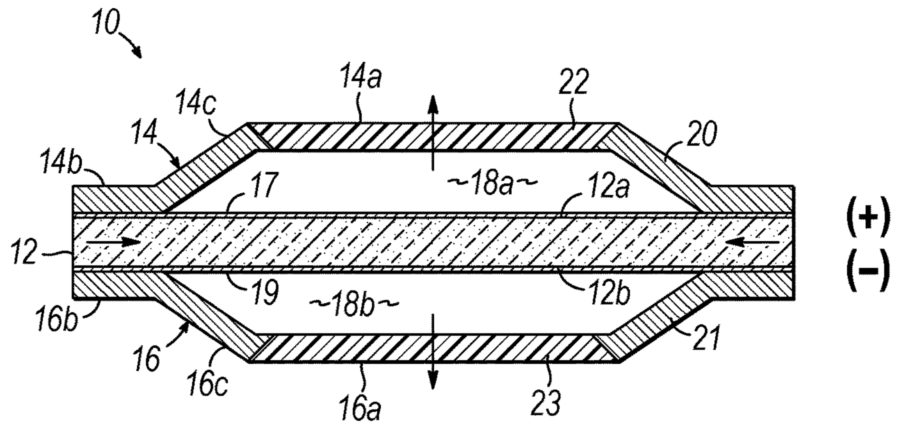
FIG. 1 is a cross-sectional view of a flextensional transducer according to one embodiment of the invention, and showing a voltage of one polarity being applied to a first electrode of the transducer and a voltage of an opposite polarity being applied to a second electrode of the transducer, causing the endcaps to flex outwardly.
Figure 2:
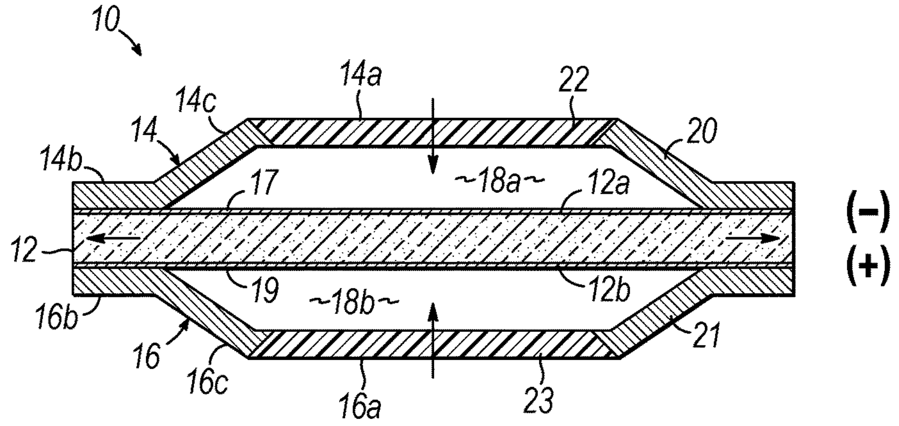
FIG. 2 is a cross-sectional view similar to FIG. 1, but showing voltages of reversed or opposite polarities being applied to the electrodes and causing the endcaps to flex inwardly.
Figure 1A:
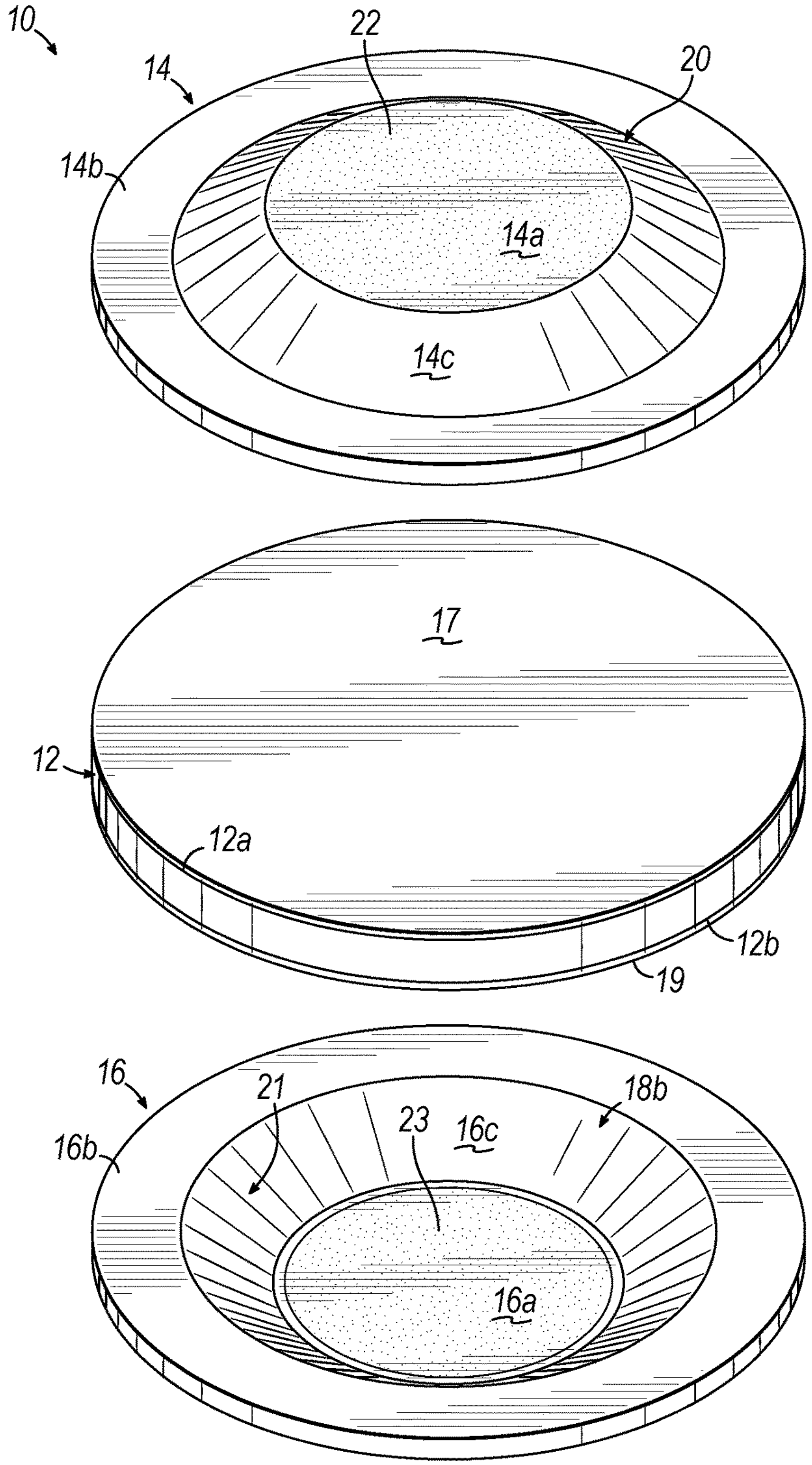
FIG. 1A is an exploded view of the flextensional transducer of FIG. 1.

With reference to FIGS. 1, 1A, 2 and in accordance with an embodiment of the invention, a flextensional transducer 10 includes a piezoelectric element 12, an endcap 14, and an endcap 16 that are coupled together to form a transducer assembly. The piezoelectric element 12 may have opposed surfaces 12*a*, 12*b* and may be arranged between the opposed endcaps 14, 16. The piezoelectric element 12 may be solid and circularly or radially symmetric (e.g., disk-shaped) relative to a central axis in a plane parallel to the surfaces 12*a*, 12*b*. The piezoelectric element 12 may be comprised of a ceramic material (e.g., a permanently-polarized material such as quartz ($SiO_2$), lead zirconate titanate (PZT), or barium titanate ($BaTiO_3$)) that is capable of converting an electrical signal into mechanical vibrations.

The piezoelectric element 12 is provided with electrodes 17 and 19, which may be disposed on the opposed surfaces 12*a*, 12*b* of the piezoelectric element 12. The electrodes 17, 19 may be composed of a conductor, such as silver (Ag), that is applied as a coating onto the opposed surfaces 12*a*, 12*b*. In particular, the electrode 17 may be applied to cover the entirety of surface 12*a* and electrode 19 may be applied to cover the entirety of surface 12*b*, such that the entirety of piezoelectric element 12 may be energized by the electrodes 17, 19, as described below.

The endcaps 14, 16 may be circularly or radially symmetric (e.g., round) relative to the central axis in the plane parallel to the surfaces 12*a*, 12*b*, and may have an outer diameter equal to the outer diameter of the piezoelectric element 12. In an embodiment, each of the endcaps 14, 16 may be formed with a truncated-conical, or cymbal-like, shape. Endcap 14 may comprise a plurality of sections that include an inner section 14*a*, an outer section 14*b*, and an intermediate section 14*c* spanning between and connecting the inner section 14*a* and outer section 14*b*. The inner section 14*a* may be planar and centrally located relative to the outer section 14*b*, the outer section 14*b* may be planar, and the intermediate section 14*c* may be angled or inclined relative to planes containing the inner and outer surfaces of sections 14*a*, 14*b*. Similarly, endcap 16 may comprise a plurality of sections that include an inner section 16*a*, an outer section 16*b*, and an intermediate section 16*c* spanning between and connecting the inner section 16*a* and outer section 16*b*. The inner section 16*a* may be planar and centrally located relative to the outer section 16*b*, the outer section 16*b* may be planar, and the intermediate section 16*c* may be angled or inclined relative to planes containing the inner and outer surfaces of sections 16*a*, 16*b*.

The opposite inner and outer surfaces of the inner sections 14*a*, 16*a* and outer sections 14*b*, 16*b* may contained in planes that are parallel to the respective planes containing surfaces 12*a*, 12*b* of the piezoelectric element 12. The inner and outer surfaces of the inner section 14*a* and the inner and outer surfaces of the outer section 14*b* of endcap 14 may be contained in planes that are parallel to the planes containing the respective inner and outer surfaces of the inner section 16*a* and outer section 16*b* of endcap 16. In an embodiment, the endcaps 14, 16 may have a uniform thickness that is location independent across the surface area, and may have equal surface areas. In an alternative embodiment, one or both of the inner sections 14, 16*a* may be thinner near its center than at its respective edges proximate intermediate sections 14*c*, 16*c*. In an alternative embodiment, one or both of the inner sections 14, 16*a* may be thicker near its center than at its respective edges proximate intermediate sections 14*c*, 16*c*. In an alternative embodiment, one or both of the inner sections 14, 16*a* may be slightly curved or bowed inwardly or outwardly (i.e., convex or concave) with a given curvature.

The endcaps 14 and 16 may have inner surfaces that are attached to the respective confronting surfaces 12*a*, 12*b* of the piezoelectric element 12. In one embodiment, the endcaps 14, 16 may have a direct attachment to the respective surfaces 12*a*, 12*b* of the piezoelectric element 12 and the electrodes 17, 19 provided thereon. As such, the endcaps 14, 16, in contact with the respective electrodes 17, 19 on the surfaces 12*a*, 12*b*, may operate as electrical contacts. Alternatively, the electrodes 17, 19 may be omitted from the area of the surfaces 12*a*, 12*b* of the piezoelectric element 12 that is attached to the endcaps 14, 16, and the electrical contacts may be established with the electrodes 17, 19 in an alternative fashion. In an embodiment, the outer section 14*b* of endcap 14 and the outer section 16*b* of endcap 16 may be respectively attached to the opposed surfaces 12*a*, 12*b* of the piezoelectric 12 at locations near the outer diameter of the piezoelectric element 12. The attachment between the endcaps 14, 16 and the piezoelectric element 12 may be created with any suitable adhesive material, such as epoxy or an electrically-conductive epoxy.

The endcap 14 may be oriented in space to be generally concave with respect to the plane containing the surface 12*a* of the piezoelectric element 12. The inner section 14*a* of endcap 14 may be spaced from the nearby surface 12*a* of the piezoelectric element 12 to establish a non-contacting relationship for section 14*a*. A cavity 18*a* is disposed between an inner surface of the endcap 14 and the adjacent opposed surface 12*a* of the piezoelectric element 12. The endcap 16 may be oriented in space to be generally concave with respect to the plane containing the surface 12*b* of the piezoelectric element 12. The inner section 16*a* of endcap 16 may likewise be spaced from the nearby surface 12*b* of the piezoelectric element 12 to establish a non-contacting relationship for section 16*a*. A cavity 18*b* is disposed between an inner surface of the endcap 14, 16 and the adjacent opposed surface 12*b* of the piezoelectric element 12. The cavities 18*a*, 18*b* may be filled with air or another gas at atmospheric pressure. The inclination of the intermediate sections 14*c*, 16*c* permits the inner sections 14*a*, 16*a* to be spaced away from the surfaces 12*a*, 12*b* and to thereby be in the respective non-contacting relationships.

In use, the piezoelectric element 12 responds to an applied electric field from an alternating current signal generated by a controlled power supply and applied as a voltage to the electrodes 17, 19 by reversibly changing its dimensions with a frequency equal to the frequency of the alternating current. As shown in FIG. 1, the material of the piezoelectric element 12 may polarized such that when a voltage of positive polarity is applied to the electrode 17 on surface 12*a* and a voltage of negative polarity is applied to the electrode 19 on surface 12*b*, the resulting electric field causes the piezoelectric element 12 to contract in a radial direction, as shown diagrammatically by the radially inward directed single-headed arrows in FIG. 1. This radial motion of the piezoelectric element 12 is mechanically transferred to the endcaps 14, 16, which in turn deform or flex outwardly in an axial direction, as shown diagrammatically by the axially outward directed single-headed arrows in FIG. 1, relative to the respective surfaces 12*a*, 12*b*. In this outward flexure mode, the spacing between the endcap 14 and surface 12*a* may increase and the spacing between the endcap 16 and surface 12*b* may increase.

As shown in FIG. 2, when voltages of reversed or opposite polarity to that of FIG. 1 are applied from the controlled power supply to the electrodes 17, 19, the direction of the electric field applied to the piezoelectric element 12 is reversed. In response to the reversed polarity voltages, the piezoelectric element 12 expands in a radial direction, which causes the endcaps 14, 16 to deform or flex inwardly in an axial direction, as shown diagrammatically by the radial inward directed single-headed arrows in FIG. 2, relative to the respective surfaces 12*a*, 12*b*. In this inward flexure mode, the spacing between the endcap 14 and surface 12*a* may increase and the spacing between the endcap 16 and surface 12*b* may decrease.

The rapid and cyclic radial expansion and contraction of the piezoelectric element 12 over a relatively small range of motion in response to the application of the alternating current signal supplied to the electrodes 17, 19 results in rapid alternating deformation or flexing in respective axial directions of the endcaps 14, 16. The rapid alternating deformation or flexing may be described as a sinusoidal motion. The rapid alternating flexing of the endcaps 14, 16 acts to emit or radiate acoustic or ultrasonic sound energy from endcap 14 outwardly in an axial direction and from endcap 16 outwardly in an axial direction, preferably from one or the other toward a target object (not shown).

The radiated sound energy, which is the product of the conversion of electrical energy to mechanical energy by the piezoelectric element 12, may be allowed to interact with the tissue of a patient and/or a substance on a tissue surface in order to provide a therapeutic effect and/or diagnostic effect. A coupling medium may be provided between one or the other of the endcaps 14, 16 and the tissue surface that promotes the efficient transfer of the radiated sound energy.

In one embodiment, the outer section 14*b* and the intermediate section 14*c* may be formed integrally as one piece so as to define an outer portion 20 of the endcap 14, and the outer section 16*b* and the intermediate section 16*c* may be formed integrally as one piece so as to define an outer portion 21 of the endcap 16. The outer portion 20 may be annular and may radially surround the inner section 14*a*, and the outer portion 21 may be annular and may radially surround the inner section 16*a*.

The endcaps 14, 16 may be composite structures that are comprised of sections of materials characterized by different mechanical properties, such as a combination of a metal section and a polymer section. To that end, the inner section 14*a* of endcap 14 may include an insert 22 and the inner section 16*b* of endcap 16 may include an insert 23. Additionally, as shown, each insert 22, 23 may be formed with a chamfer at its outer diameter to enable effective mating and bonding with a corresponding chamfered surface at the inner diameter of the corresponding radially outer portion 20, 21. The inserts 22, 23 may be composed of a material that is different in its mechanical properties (e.g., more flexible than) from the material composing the corresponding outer portion 20, 21. In one embodiment, the inserts 22, 23 may be comprised of a polymer, such as polyurethane or polycarbonate. The outer portions 20, 21 may be formed of any suitable metal such as brass, aluminum, or stainless steel, and may be easily manufactured by, for example, punching sheet metal. If formed from a metal, the outer portions 20, 21 may provide for a robust endcap structure and a strong mechanical coupling between the endcaps 14, 16 and the piezoelectric element 12. In alternative embodiments, the endcaps 14, 16 may be formed without inserts 22, 23, and may be comprised in their entirety from a polymer and metal-free, or comprised in their entirety from a metal and polymer-free.

With continued reference to FIGS. 1 and 2, when the piezoelectric element 12 is energized by the alternating current signal applied to the electrodes 17, 19, the mechanical movement of the piezoelectric element 12 is transferred to the endcaps 14, 16 and, in particular, to the inserts 22, 23 of the endcaps 14, 16, which may flex axially in a "trampoline" mode of motion. The flexibility of the inserts 22, 23 may allow for a greater degree of mechanical deformation (e.g., a larger displacement in a direction perpendicular to the plane of the opposed surfaces 12*a*, 12*b* of the piezoelectric element 12 when excited by the application of the alternating current signal to the electrodes 17, 19) than otherwise provided by endcaps formed solely of a metal (i.e., a more rigid design). Accordingly, if constructed from a flexible and non-metallic material, the inserts 22, 23 may enable the inner sections 14*a*, 16*a* of the endcaps 14, 16 to flex with a greater displacement than the respective outer portions 20, 21 composed of a metal of higher stiffness. The non-metallic material forming the inserts 22, 23 may be additionally superior to metal in this application in that it may provide a closer acoustic impedance match with the bodily skin or tissue of a medical patient, and thereby may improve energy transfer from the transducer 10 to skin or tissue. The rigidity of outer portions 20, 21 comprised of a metal may stiffen the composite endcap structure including compensating for any reduction in stiffness introduced by the inserts 22.

The flextensional transducer 10 comprised of the assembly of the endcaps 14, 16 and the piezoelectric element 12 operates as a mechanical amplifier having a resonance frequency with the piezoelectric element 12 functioning as an actuator. This resonance frequency of the flextensional transducer 10 may be tuned by adjusting various design parameters of its individual components, including the piezoelectric element 12, the inserts 22, 23, and/or the outer portions 20, 21 of the endcaps 14, 16. For example, design parameters corresponding to the inserts 22, 23 may include material type, which dictates material properties such as stiffness and/or density, and physical dimensions such as diameter or thickness. Design parameters corresponding to the outer portions 20, 21 may include material type and physical configuration, including dimensions and shape. For example, physical configuration factors may include area of contact between the outer portion 20, 21 and the piezoelectric element 12, endcap height (i.e., in an axial direction normal to surfaces 12*a*, 12*b*), endcap thickness, and angle of slope of the intermediate section 14*c*, 16*c*. Design parameters corresponding to the piezoelectric element 12 may include material type and physical dimensions. In this regard, and as described in greater detail below, the resonance frequency of a piezoelectric element having a solid disk shape is generally proportional to its radiating surface area, which may be adjusted in size to effectively tune the resonance frequency of the piezoelectric element, and thus the resonance frequency of the assembled transducer. The transducer 10 may be tuned with the aid of simulation tools such as COMSOL Multiphysics® software. Sample simulations are described in greater detail in the Examples hereinbelow.

FIGS. 3-15B show additional flextensional transducers according to various alternative embodiments of the invention. Throughout the figures, similar reference numerals refer to similar features. General principles of flextensional transducers described above may also generally apply for the following embodiments described below.

Figure 3:
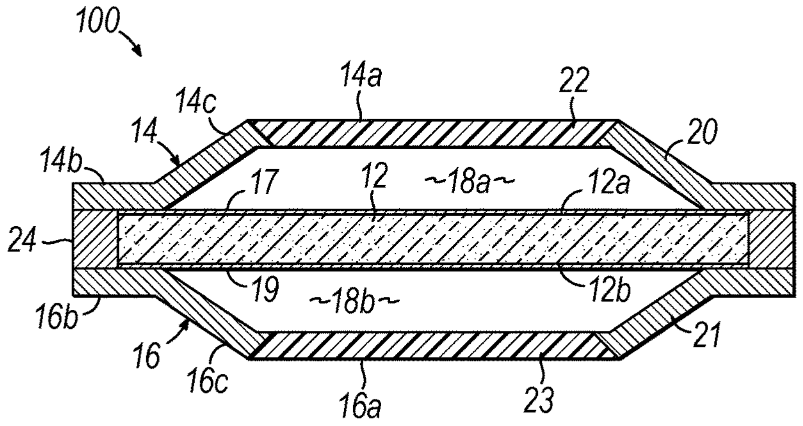
FIG. 3 is a cross-sectional view of a flextensional transducer according to another embodiment including a connecting ring to which the endcaps are attached.

With reference to FIG. 3, a flextensional transducer 100 includes a connecting ring 24 having an inner circumference, or inner diameter, that abuts the side edge of the piezoelectric element 12 at its outer circumference or outer diameter. The ring 24 may be applied to the piezoelectric element 12 by first heating the ring 24 so that it thermally expands outwardly in a radial direction, and then placing ring 24 around the piezoelectric element 12 and allowing it to cool and contract to form a friction connection with the piezoelectric element 12. Alternatively, the piezoelectric element 12 may first be cooled so that it shrinks, and may then be placed within the ring 24 and permitted to expand to form a friction connection with the ring 24. The connecting ring 24 may be formed with an axial thickness that is substantially equal to an axial thickness of the piezoelectric element 12.

The endcaps 14, 16 may be attached to the connecting ring 24 by an adhesive bond or by mechanical fasteners, which may include bolts or screws, rather than being attached to the piezoelectric element 12. In one embodiment, the endcaps 14, 16 may be directly attached to the connecting ring 24 and lack any attachment to the piezoelectric element 12. When an alternating current is applied to the electrodes 17, 19, the ring 24 expands and contracts radially along with the piezoelectric element 12 and transfers this motion (i.e., the expansion and contraction) to the endcaps 14, 16.

The use of connecting ring 24 may allow for a more mechanically robust coupling of the endcaps 14, 16 with the piezoelectric element 12. In particular, the attachment between the endcaps 14, 16 and the ring 24 may be more resilient than an adhesive bonding of the endcaps 14, 16 directly to the piezoelectric element 12, which might otherwise fail prematurely under shear stresses experienced during rapid alternating expansions and contractions of the piezoelectric element 12 when in use. The connecting ring 24 or a similar structure, including the dual connecting ring 40 described below, may be incorporated as appropriate into any of the embodiments of the flextensional transducers described herein.

Figure 4:
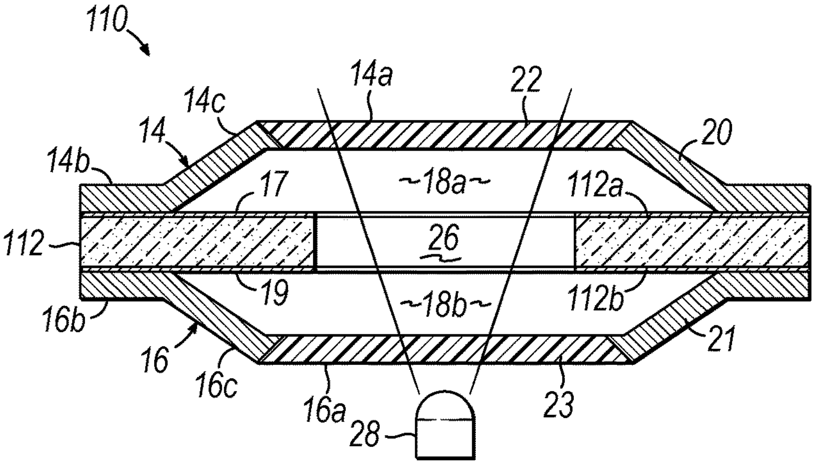
FIG. 4 is a cross-sectional view of a flextensional transducer according to another embodiment similar to that shown in FIG. 1, but including an annular piezoelectric element having a central aperture through which light may be transmitted.

With reference to FIG. 4, a flextensional transducer 110 includes a piezoelectric element 112 with an aperture 26 penetrating or passing therethrough in an axial direction. The piezoelectric element 112 may be annular, disk-shaped, and the aperture 26 may be centrally located in the piezoelectric element 112. The electrodes 17, 19 are applied to the opposed surfaces 112*a*, 112*b*. The piezoelectric element 112 has a side surface with an outer circumference or diameter, and a side surface with an inner circumference or inner diameter that is coextensive with the aperture 26.

The resonance frequencies of the flextensional transducers described herein having disk-shaped piezoelectric elements may be tuned, even if only nominally, by adjusting the size of the radiating area of the corresponding piezoelectric element. For example, with reference to transducer 110, such tuning of the transducer may be achieved by adjusting the outer diameter of the piezoelectric element 12 so as to increase or decrease the areas of surfaces 12*a* and 12*b*. With reference to transducers including annular piezoelectric element 112, such as transducer 110, tuning of the transducer may be achieved by adjusting the inner and outer diameters of the piezoelectric element 112, and more specifically, increasing or decreasing the difference between these two diameters to as to vary the areas of annular surfaces 112*a* and 112*b*.

A light source 28 may be positioned adjacent or otherwise proximate one of the endcaps 14, 16 and aimed such that light may be transmitted through the flextensional transducer 110 in an axial direction and onto a target object, such as the skin or tissue of a medical patient, positioned adjacent the opposite endcap 14, 16. For example, as shown in FIG. 4, the light source 28 may be positioned adjacent to the endcap 16 and energized to transmit light through the central insert 23 disposed thereon, through the aperture 26, through the insert 22 disposed on the endcap 14, and onto the skin or tissue of a patient positioned adjacent the endcap 14.

The addition of the aperture 26, in combination with the inserts 22, 23 of the endcaps 14, 16, promotes the transmission of light from the light source 28 through the flextensional transducer 110, as diagrammatically shown in FIG. 4. The inserts 22, 23 may be transparent, translucent, or otherwise capable of allowing at least some light emitted by the light source 28 to pass therethrough in an axial direction, and the aperture 26 provides an optical path for light to travel unimpeded through the piezoelectric element 112. In an embodiment, the term "light" may refer to any wavelength of light in the visible, ultraviolet (UV), infrared (IR), or nearby wavelengths of the electromagnetic spectrum. The light transmission may occur with low loss due to scattering, absorption, etc. in the medium comprising the inserts 22, 23. The light source 28 may be separate from or incorporated into the structure of the flextensional transducer 110, and may take the form of a laser, an incandescent light, a light emitting diode (LED), an excimer lamp, or any other narrowband or wideband light source.

With any described embodiment herein having a transparent or translucent central insert, the transducer may operate to expose the target object to both ultrasound and light stimulation either simultaneously or in a rapidly alternating pattern, which may include pulsations. For tissue, the light exposure may cause a therapeutic treatment and/or may elicit a photoacoustic response from the tissue such that the resultant ultrasound wave is detectable using the transducer as a receiver.

Exposure to both optical and ultrasound energy may be advantageous in the treatment of various conditions of the skin and dermis, including acne, surgical and non-surgical wounds, melanomas, and other conditions and diseases. The simultaneous or successive application of ultrasound and therapeutic light treatment to the same tissue volume may be achieved without the use of a separate faceplate.

Simultaneous, sequential, or overlapping exposure to light and ultrasound stimulation using the flextensional transducers described herein may also be advantageous in the treatment of biofilms. The emitted ultrasound (i.e., ultrasonic energy) may cause an activation of bacteria (which increases the susceptibility of the bacteria to antibiotics), a degradation of the biofilm coating (which also increases the susceptibility of the bacteria to antibiotics), and an antibacterial effect if the light has the proper wavelength (typically in the blue to ultraviolet range, either broadband or narrowband). Ultrasound alone may exhibit an effect on biofilms, and may be advantageous particularly when the biofilm is located at a depth beyond that treatable by light. This effect may occur where there is scattering and absorption by overlying tissues or structures, such as breast implants or other implants, catheters, heart valves, and orthopedic devices for the hip, shoulder, or other body portions.

Figure 5A:
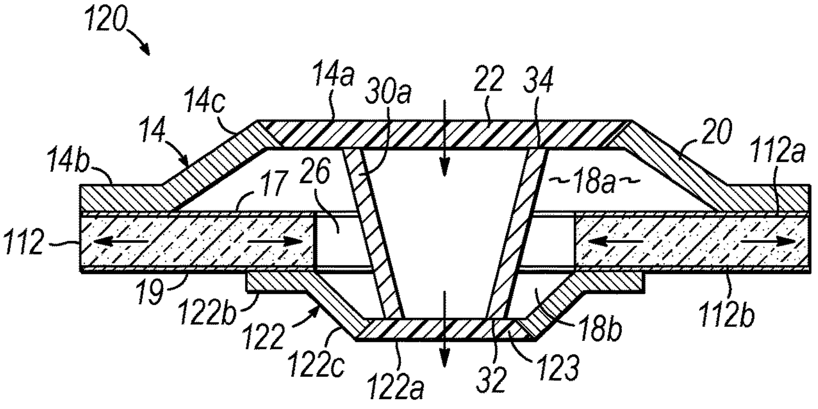
FIG. 5A is a cross-sectional view of a flextensional transducer according to another embodiment similar to that shown in FIG. 4, but including first and second endcaps of different diameters and a hollow coupling element that couples the endcaps to one another.

With reference to FIG. 5A, a flextensional transducer 120 includes endcaps having different outer diameters and that are bonded to an annular piezoelectric element 112 at non-overlapping radial distances. In particular, as shown, the transducer 120 includes an endcap 122 having physical dimensions, including an outer diameter and an endcap height, that are less than the comparable physical dimensions of the large endcap 14. However, the smaller endcap 122 may be formed with a material composition and method of manufacture similar to those described above in connection with endcaps 14, 16. In that regard, the small endcap 122 may include an insert 123 that is similar in material composition and construction, as well as function, to that of inserts 22, 23 described above. The small endcap 122 may be bonded to the annular piezoelectric element 112 at a location near the inner circumference, or inner diameter, of the piezoelectric element 112, and the large endcap 16 may be bonded to the piezoelectric element 112 at a location near the outer circumference, or outer diameter, of the piezoelectric element 112. Additionally, while the transducer 120 is shown oriented such that the small endcap 122 is located on a bottom side of the transducer 120, the transducer 120 may be reoriented as desired such that the small endcap 122 is located on a top side of the transducer 120.

When the annular piezoelectric element 112 is energized, it expands radially outward at its outer diameter and radially inward at its inner diameter, as shown diagrammatically by the single-headed arrows in FIG. 5A. Consequently, the large endcap 14, including insert 22, flexes axially inward while the small endcap 122, including insert 123, flexes axially outward such that both endcaps 14, 122 simultaneously flex in the same direction, as shown diagrammatically by the single-headed arrows. This coordinated directionality of the flexing may impart a directionality to the ultrasonic energy emitted from the transducer 120, and may reduce wasted ultrasonic energy so that the emission of ultrasonic energy may be maximized. Acoustic energy that would otherwise propagate in a direction away from the patient may be redirected back towards the patient.

The flextensional transducer 120 may further include a coupling element 30*a* centrally disposed in the aperture 26. The coupling element 30 mechanically couples the large endcap 14 with the small endcap 122 and thereby increases the ultrasound energy directed to, or a force exerted on, a target object positioned adjacent the large endcap 14. In the representative embodiment, the coupling element 30 mechanically couples the insert 22 of large endcap 14 with the insert 123 of small endcap 122. The coupling element 30*a* may have a hollow construction with a trapezoidal-shaped cross-section defining a small end 32 abutting an internal surface of the small endcap 122 and a large end 34 abutting an internal surface of the large endcap 14. The inner diameter of the coupling element 30*a* tapers in a direction from the large end 34 to the small end 32. Additionally, the coupling element 30*a*, as well as the alternative coupling elements described below, may be formed of any suitable material, such as a polymer.

Figure 5B:
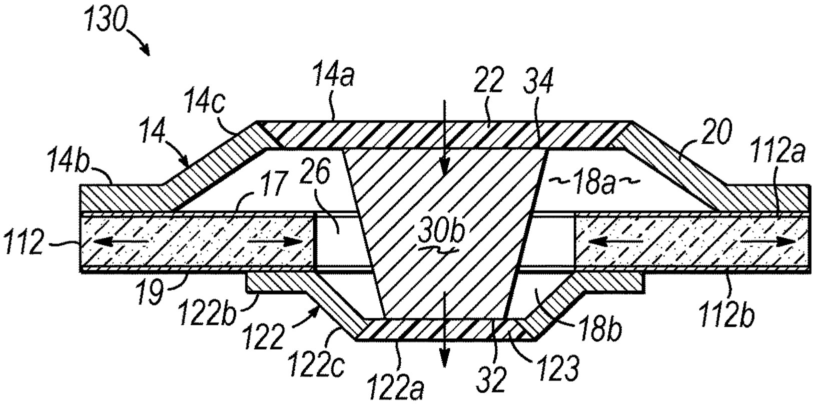
FIG. 5B is a cross-sectional view of a flextensional transducer according to another embodiment similar to that shown in FIG. 5A, but including a solid coupling element.

With reference to FIG. 5B, a flextensional transducer 130 is similar in construction to transducer 120, but may include a coupling element 30*b* having a solid construction rather than a hollow construction. In this regard, each end 32, 34 may be sized appropriately to increase the surface area of the connection or contact between the coupling element 30*b* and each endcap 14, 122 in comparison with the hollow version of the coupling element 30*a*.

Figure 5C:
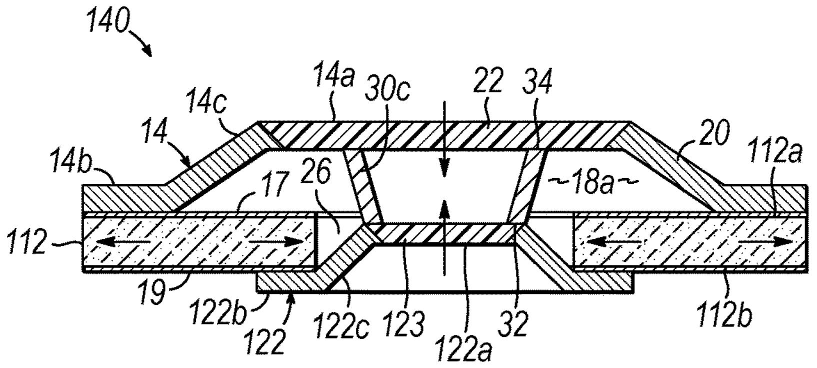
FIG. 5C is a cross-sectional view of a flextensional transducer according to another embodiment similar to that shown in FIG. 5A, but including a small diameter endcap that is attached in an inverted orientation to the piezoelectric ceramic element.

With reference to FIG. 5C, a flextensional transducer 140 is similar in construction to transducers 120 and 130, but the small endcap 122 is attached in an inverted orientation to the annular piezoelectric element 11 in comparison with FIG. 5B. A portion of the small endcap 122 is disposed within or projects into the aperture 26. With this configuration, the concavities of the endcaps 14, 122 have the same orientation relative to each other. More specifically, the large endcap 14 is concave relative to a plane defined by the surface of the piezoelectric element 112 to which it is attached, and the small endcap 122 is convex relative to the plane defined by the surface of the piezoelectric element 112 to which it is attached.

When the piezoelectric element 112 is energized and expands in its radial directions, as shown by the single-headed arrows in FIG. 5C, the endcaps 14, 122 each flex axially inward toward one another. Consequently, sound energy radiates outwardly from both sides of the transducer 150, but the design of the transducer 150 is kept axially compact. The transducer 140 may further include a hollow coupling element 30*c* that is shorter in length than the coupling elements 30*a*, 30*b* due to a decreased distance between the endcaps 14, 122 produced by the inverted orientation of the small endcap 122.

Figure 5D:
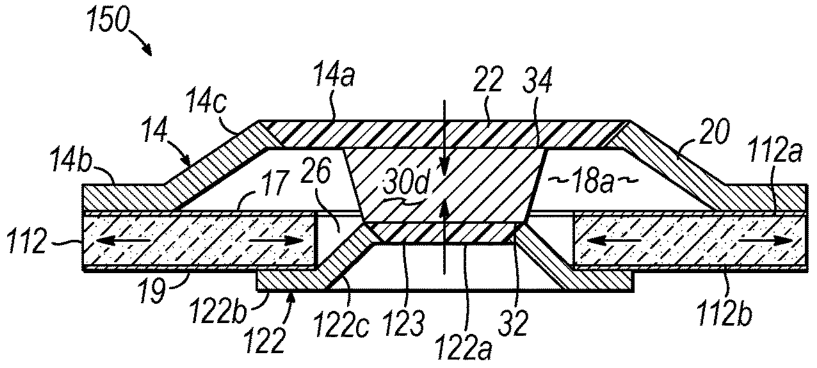
FIG. 5D is a cross-sectional view of a flextensional transducer according to another embodiment similar to that shown in FIG. 5C, but including a solid coupling element.

With reference to FIG. 5D, a flextensional transducer 150 is similar in construction to transducer 140 described above, but may include a coupling element 30*d* having a solid construction rather than a hollow construction.

In alternative embodiments to FIGS. 5A-5D, the coupling element may be omitted from the construction of the flextensional transducer. Additionally, in other embodiments, the construction of each endcap 14, 122 may be integral (i.e., a single piece) and formed solely of a metal in order to provide robust surfaces for attachment to a coupling element, or the endcaps 14, 122 may be formed solely of a single polymer material.

Figure 6A:
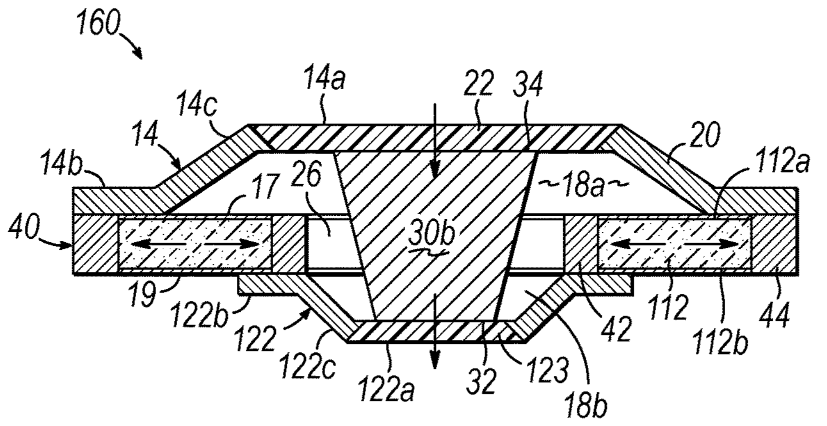
FIG. 6A is a cross-sectional view of a flextensional transducer according to another embodiment similar to that shown in FIG. 5B, but including a dual connecting ring to which the endcaps are attached.

With reference to FIG. 6A, a flextensional transducer 160 is similar in construction to transducer 130 described above, but may include a dual connecting ring system 40 having an inner ring 42 and an outer ring 44 for mechanically coupling the annular piezoelectric element 112 with the endcaps 14, 122. As shown, the inner ring 42 abuts an inner circumference of the piezoelectric element 112 while the outer ring 44 abuts an outer circumference of the piezoelectric element 112. The inner and outer rings 42, 44 may be formed with axial thicknesses that are substantially equal to an axial thickness of the piezoelectric element 112.

The inner and outer rings 42, 44 of the dual connecting ring system 40 may be connected to the piezoelectric element 112 using the same methods described above with respect to connecting ring 24 of transducer 100. For example, the inner ring 42 may first be cooled so that it contracts radially, and may then be placed within the inner circumference of the piezoelectric element 112 and permitted to expand to form a friction connection therewith. The outer ring 44 may then be heated so that it thermally expands radially, and may then be placed around the outer circumference of the piezoelectric element 112 and permitted to cool and contract to form a friction connection therewith. As described above with respect to transducer 100, the endcaps 14, 122 may be coupled to the outer and inner rings 42, 44, respectively, by an adhesive bond or by mechanical fastening. The dual connecting ring system 40 may provide benefits similar to those described above with respect to connecting ring 24.

Figure 6B:
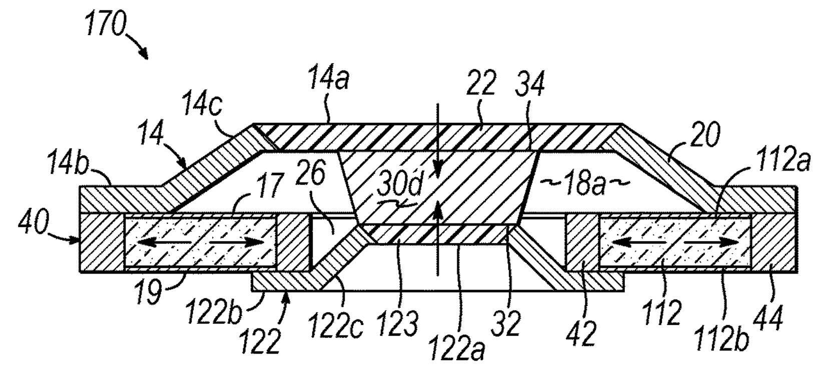
FIG. 6B is a cross-sectional view of a flextensional transducer according to another embodiment similar to that shown in FIG. 6A, but including a small diameter endcap that is attached in an inverted orientation to the dual connecting ring.

With reference to FIG. 6B, a flextensional transducer 170 is similar in construction to transducer 160 described above, but the small endcap 122 may be attached in an inverted orientation to the annular piezoelectric element 112 in a manner similar to that described above in connection with transducer 140.

Figure 7:
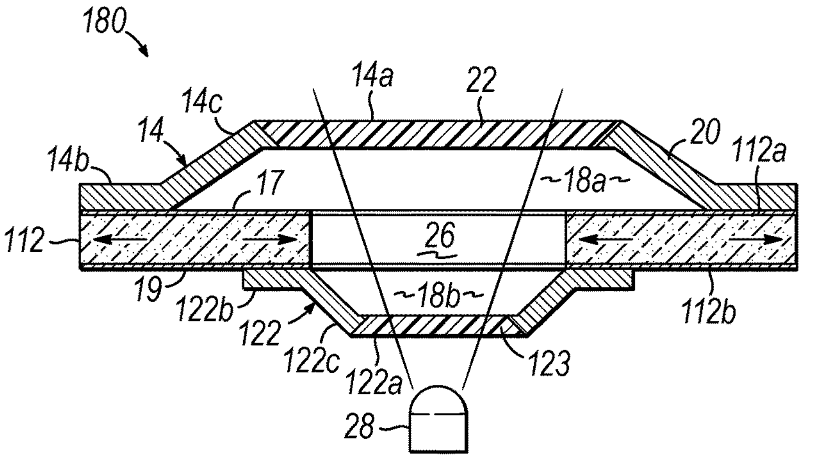
FIG. 7 is a cross-sectional view similar of a flextensional transducer according to another embodiment similar to those shown in FIGS. 5A and 5B, but excluding a coupling element and showing light being transmitted through the transducer.

With reference to FIG. 7, a flextensional transducer 180 is similar in construction to transducer 120 described above, but lacks a coupling element positioned between the endcaps 14, 122. The inserts 22, 123 of the endcaps 14, 122 may be formed of a transparent or translucent polymer material, as described above, so that light may be transmitted therethrough. As shown, the light source 28 may be positioned adjacent the small endcap 122 to transmit light through the transducer 180 and provide light stimulation to skin or tissue of a medical patient positioned adjacent the large endcap 14. The patient may thus receive both optical energy and ultrasonic energy simultaneously or in a rapidly alternating pattern, as described above, for therapeutic purposes that may originate from synergistic effects.

Figure 8:
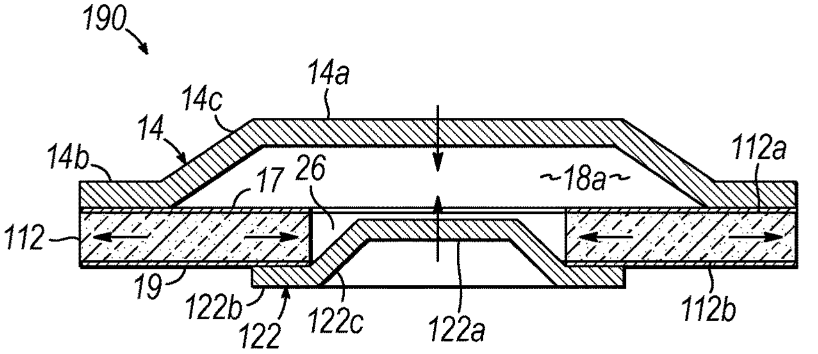
FIG. 8 is a cross-sectional view of a flextensional transducer according to another embodiment including an annular piezoelectric element and first and second endcaps of different diameters attached thereto, where the small diameter endcap is attached in an inverted orientation.

With reference to FIG. 8, a flextensional transducer 190 is similar in construction to transducer 140, but lacks a coupling element positioned between the endcaps 14, 122, and does not include inserts 22, 123 within the endcaps 14, 122. As shown, each endcap 14, 122 is formed as a single integral piece, and may be comprised entirely of a single material, such as a metal or a polymer, for example.

Figure 9:
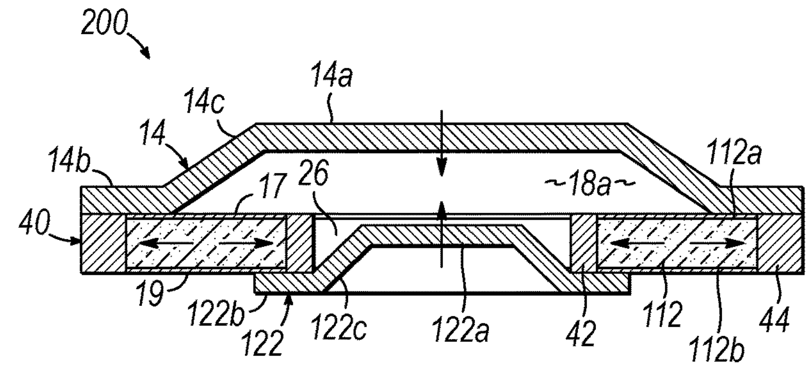
FIG. 9 is a cross-sectional view of a flextensional transducer according to another embodiment similar to that shown in FIG. 8, but including a dual connecting ring to which the endcaps are attached.

With reference to FIG. 9, a flextensional transducer 200 is similar in construction to transducer 190, but includes the dual connecting ring 40 described above in connection with FIG. 6A. The transducers 190 and 200, while shown having endcaps 14, 122 formed as single integral pieces, may be modified to include the transparent or translucent inserts 22, 123.

Figure 10:
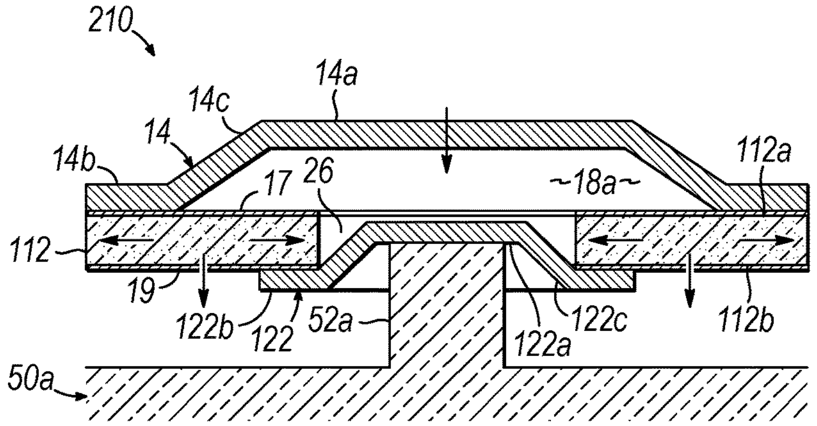
FIG. 10 is a cross-sectional view of a flextensional transducer according to another embodiment similar to that shown in FIG. 8, showing the small diameter endcap attached to a support structure.

With reference to FIG. 10, a flextensional transducer 210 is similar in construction to transducer 190, and is rigidly attached to and secured by a stationary support structure 50*a*. The support structure 50*a* may include a protruding anchor portion 52*a* to which an inner section 122*a* of the small endcap 122 may be secured. The small endcap 122 may be secured to the anchor portion 52 by any suitable means, such as adhesive bonding or mechanical fastening, for example. Additionally, as shown, the small endcap 122 may be formed as a single integral piece without insert 123, thereby providing a rigid surface for attachment to the anchor portion 52*a*. When the annular piezoelectric element 112 is energized and expands in its radial directions, the inner section 122*a* of the small endcap 122 is restrained from moving axially relative to the support structure 50*a*, thus forcing the entire transducer 210 to move as a unit in an axial direction and relative to the support structure 50*a*. Accordingly, all sound energy generated by the transducer 210 is emitted in a direction opposite from the support structure 50*a*.

The stationary support structures 50*a*, 50*b*, and 50*c* described herein in connection with various embodiments may be composed of any suitable material, such as a metal, a polymer, or a composite material, for example. Additionally, the stationary support structures 50*a*, 50*b*, 50*c* may be sufficiently massive to overcome the reaction mass of the corresponding piezoelectric element 112, 212 during movement thereof, and thereby remain stationary during operation of the transducer.

Figure 11:
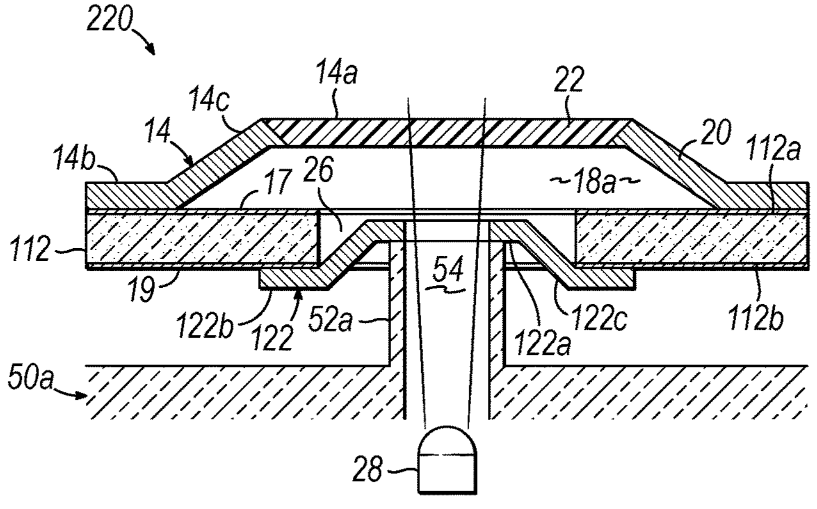
FIG. 11 is a cross-sectional view of a flextensional transducer according to another embodiment similar to that shown in FIG. 10, including a central aperture that extends through the support structure and the small diameter endcap, and showing light being transmitted through the support structure and the transducer.

With reference to FIG. 11, a flextensional transducer 220 is similar in construction to transducer 210, but the small endcap 122 is formed with an annular shape and the large endcap 14 includes transparent or translucent insert 22. Additionally, an aperture 54 extends axially through the anchor portion 52*a* of the supporting structure 50*a* and through the inner section 122*a* of the small endcap 122, and opens to the inner cavity 18*a*. As shown, the light source 28 may be positioned at a location adjacent to, or within, the aperture 54 such that light may be transmitted through the support structure 50*a* and transducer 220 and onto a target object located adjacent an external surface of the insert 22 of the large endcap 14. As described above, the target object, such as the tissue or skin of a medical patient, may thus be exposed to both ultrasound and light stimulation using a single device.

Figure 12:
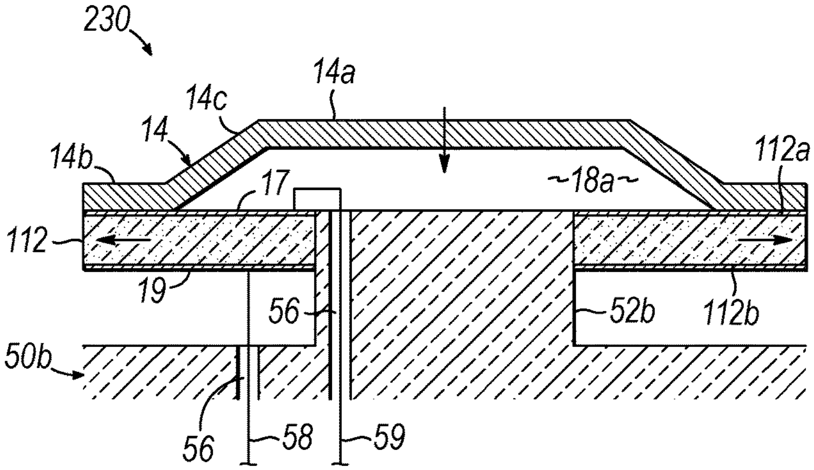
FIG. 12 is a cross-sectional view of a flextensional transducer according to another embodiment including an annular piezoelectric element attached to a support structure and a single endcap attached to the ceramic element.

With reference to FIG. 12, a flextensional transducer 230 includes a single endcap 14 from which sound energy may be emitted, and which may be formed integrally as a single piece without insert 22. The annular piezoelectric element 112 is attached at its inner circumference directly to an outer surface of an anchor portion 52*b* of a stationary support structure 50*b*. Accordingly, the inner circumference of the piezoelectric element 12 is restrained from expanding radially inward when the piezoelectric element 12 is energized. As a result, the resonance frequency of the piezoelectric element 112 of this embodiment may be intermediate to the resonance frequencies of the solid, disk-shaped piezoelectric element 12 shown in FIGS. 1-3 and of the annular, disk-shaped piezoelectric element 112 shown in FIGS. 4-11.

The resonance frequency characteristics of the transducer 230 shown in FIG. 12 may be adjusted by varying the diameter of the anchor portion 52*b*, and thereby the inner diameter of the annular piezoelectric element 112, while maintaining constant the outer diameter of the piezoelectric element 12. The transducer assembly 230 may be mechanically mounted in such a way that the ultrasound energy is maintained, and radiated away from the support structure 50*b* and towards the patient.

As shown in FIG. 12, the support structure 50*b* may include two passageways 56 extending in an axial direction and through which conductive wires 58 and 59 may be passed for electrically connecting to electrodes 17, 19 disposed on each of the opposed axial faces of the piezoelectric element 112. In this manner, at least a portion of the conductive wire 59 connected to the electrode 17 disposed within the inner cavity 18*a* may be insulated within the inner cavity 18*a* and thereby provided with better protection against vibrations. The conductive wires 58, 59 may both exit the transducer 230 on the same side.

Figure 13:
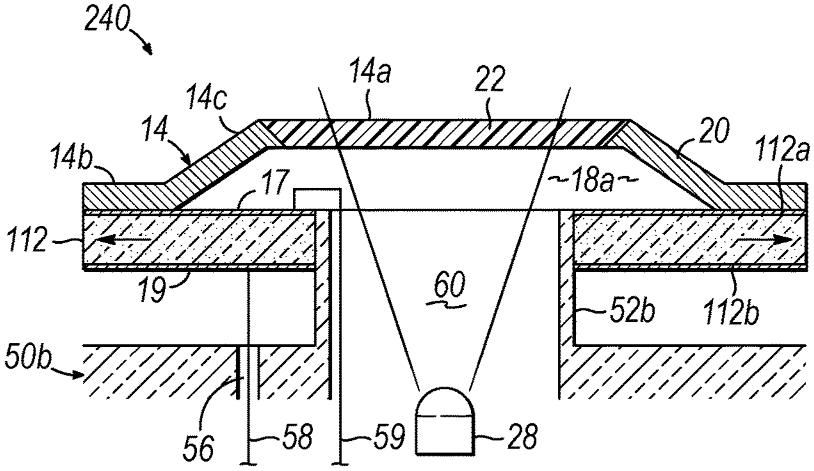
FIG. 13 is a cross-sectional view of a flextensional transducer according to another embodiment similar to that shown in FIG. 12, but including an endcap having a central insert and a central aperture that extends through the support structure, and showing light being transmitted through the support structure and transducer.

With reference to FIG. 13, a flextensional transducer 240 is similar in construction to transducer 230, but the endcap 14 further includes the transparent or translucent insert 22, and a central aperture 60 extends through the anchor portion 52*b* and opens to the inner cavity 18*a* defined by the endcap 14. Accordingly, the light source 28 may be positioned at a location adjacent to or within the central aperture 60 such that light may be transmitted through the support structure 50 and transducer 240, and onto a target object located adjacent an outer surface of the insert 22 of the endcap 14. As described above, the target object may thus be exposed to both ultrasound and light stimulation simultaneously.

The support structure 50*b* may include a passageway 56 through which conductive wire 58 may be passed for electrically connecting to the electrode 19 disposed externally to inner cavity 18*a*. The central aperture 60 may be formed with a diameter of sufficient size so that conductive wire 59 may be passed therethrough for electrically connecting to the electrode 17 disposed within the inner cavity 18*a*, without substantially interfering with the transmission of light through the aperture 60. The conductive wires 58, 59 may be coupled with an ultrasound generator circuit (e.g., waveform generator, amplifier) and a controller that are configured to control the operation of the transducer 240.

Figure 14A:
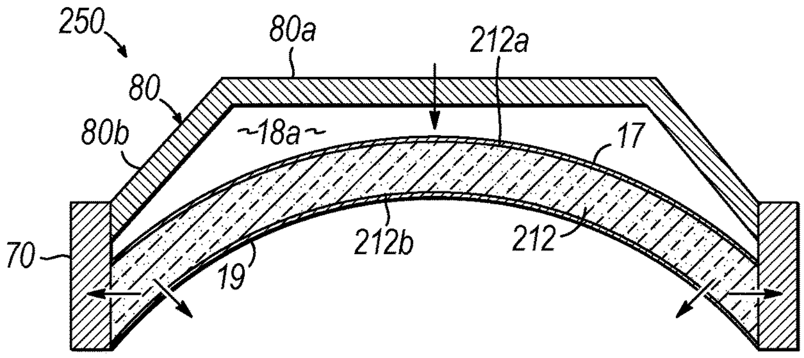
FIG. 14A is a cross-sectional view of a flextensional transducer according to another embodiment including a single endcap and a piezoelectric element having a convex shape relative to the endcap.

With reference to FIG. 14A, a flextensional transducer 250 includes a curved piezoelectric element 212 having a solid, bowl-like curved arc shape with a convex curvature, rather than a planar disk-like shape as shown in other embodiments. The convex curved piezoelectric element 212 may be radially symmetric and may be attached at its outer circumference, or outer diameter, to a radially inner surface of a connecting ring 70. This attachment between the connecting ring 70 and the piezoelectric element 212 may be formed by any suitable means, which may include a friction connection formed by thermal expansion and contraction as described above with respect to connecting ring 24. The electrodes 17, 19 are applied to the opposed surfaces 212*a*, 212*b*.

The transducer 250 may include a single endcap 80 having a central inner section 80*a* and an angled outer section 80*b*. The endcap 80 may be formed with a material composition and method of manufacture similar to those described above with respect to endcaps 14, 16. While the endcap 80 is shown in this embodiment as a single integral piece formed entirely of a single material, in alternative embodiments the endcap 80 may be formed of multiple materials and may include transparent or translucent insert 22, as described below. The angled outer section 80*b* may be attached to the same radially inner surface of the connecting ring 70 as the piezoelectric element 212, such that an inner cavity 18*a* is defined collectively by the endcap 80, the connecting ring 70, and a convex curved surface of the piezoelectric element 212. Accordingly, the connecting ring 70 may be formed with a sufficient axial thickness such that the radially inner surface of the ring 70 may attach to the endcap 80 and the piezoelectric element 212 at locations that are axially spaced from one another.

When the curved piezoelectric element 212 is energized, its curved, bowl-like shape operates to couple both radial expansion motion and flexing motion of the piezoelectric element 212 to the endcap 80. Specifically, the radial expansion or extension motion of the piezoelectric element 212 is shown in FIG. 14A by the arrows pointing in a direction perpendicular to the connecting ring 70, and the flexing motion is shown by the arrows pointing toward a focal point (not shown) of the concave curved surface of the piezoelectric element 212. In this manner, two forms of motion by the piezoelectric element 212 may be coupled to, and simultaneously contribute to, the flexing of the endcap 80.

Figure 14B:
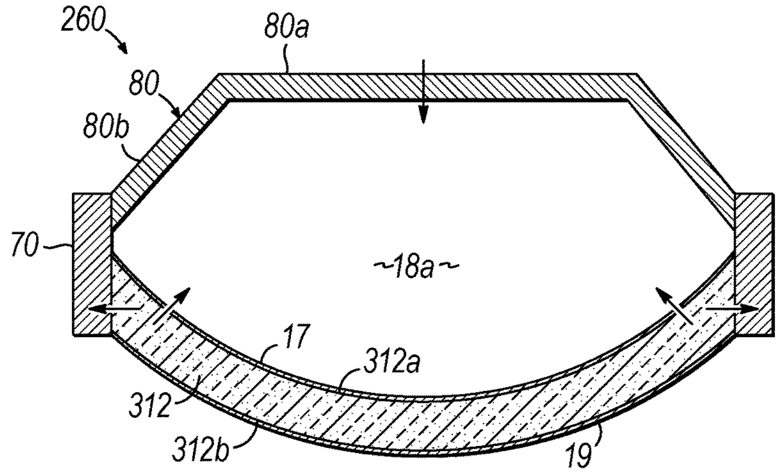
FIG. 14B is a cross-sectional view of a flextensional transducer according to another embodiment similar to that shown in FIG. 14A, but including a piezoelectric element having a concave shape relative to the endcap.

With reference to FIG. 14B, a flextensional transducer 260 according to another embodiment of the invention is shown. The transducer 260 is similar in construction to the transducer 250 described above, but includes a curved piezoelectric element 312 having a curvature opposite that of curved piezoelectric element 212. In particular, the curved piezoelectric element 213 has a solid, bowl-like shape with a concave curvature, and is attached to the connecting ring 70 such that an inner cavity 18*a* is defined collectively by the endcap 80, the connecting ring 70, and a concave curved surface of the piezoelectric element 312. Accordingly, the inner cavity 18*a* of transducer 260 may be substantially larger than the inner cavity 18*a* of transducer 250. The electrodes 17, 19 are applied to the opposed surfaces 312*a*, 312*b*.

Figure 15A:
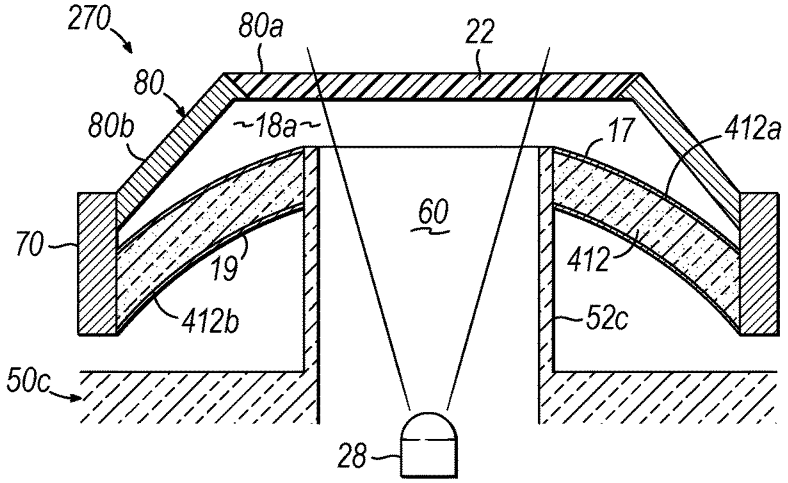
FIG. 15A is a cross-sectional view of a flextensional transducer according to another embodiment including a convex, annular piezoelectric element attached to a support structure having a central aperture, and showing light being transmitted through the support structure and the transducer.

With reference to FIG. 15A, a flextensional transducer 270 according to another embodiment of the invention is shown. The transducer 270 is similar in construction to transducer 250 described above, but includes an annular, curved piezoelectric element 412 having a convex, bowl-like shape, and is rigidly attached to and secured by a stationary support structure 50*c*. In particular, as shown, the piezoelectric element 412 may be attached at its inner circumference to an upper end of an anchor portion 52*c* of the support structure 50*c*. The electrodes 17, 19 are applied to the opposed surfaces 412*a*, 412*b*.

A central aperture 60 extends axially through the anchor portion 52*c* and opens to the inner cavity 18*a*. Additionally, the endcap 80 may include a transparent or translucent insert 22. A light source 28 may be positioned at a location adjacent to or within the central aperture 60 such that light may be transmitted through the support structure 50*c* and transducer 270 and onto a target object located adjacent an outer surface of the insert 22 of the endcap 80. In this manner, as described above, the target object may be exposed to both light and ultrasound stimulation simultaneously or intermittently.

The flextensional transducers 250 and 270 shown and described above in connection with FIGS. 14A and 15A advantageously present compact configurations that may be easily manufactured, and that may be adapted to achieve a desired resonance frequency so as to take advantage of multiple vibration modes of the curved piezoelectric elements 212, 412.

Figure 15B:
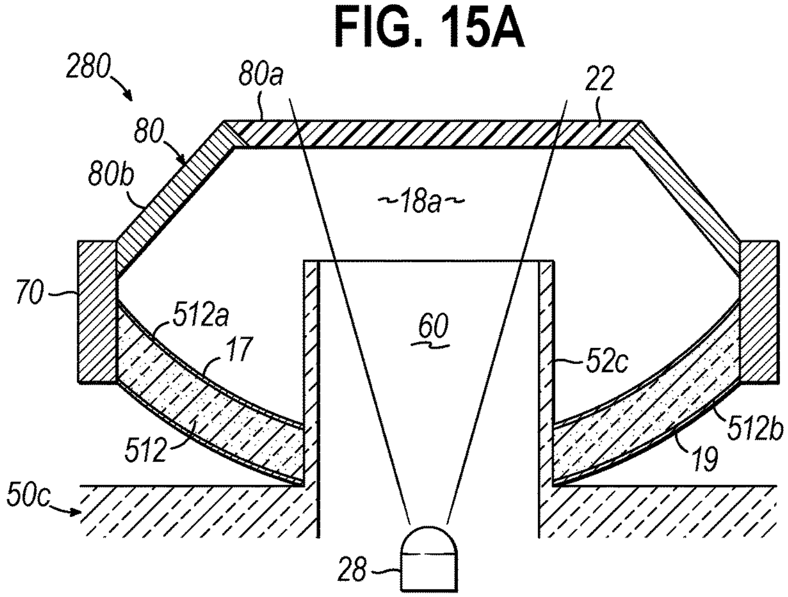
FIG. 15B is a cross-sectional view of a flextensional transducer according to another embodiment similar to that shown in FIG. 14A, but including a piezoelectric element having a concave shape relative to the endcap, and showing light being transmitted through the support structure and the transducer.

With reference to FIG. 15B, a flextensional transducer 280 according to another embodiment of the invention is shown. The transducer 280 is similar in construction to the transducer 270 described above, but includes an annular, curved piezoelectric element 512 having a curvature generally opposite that of piezoelectric element 412. For example, the curvature of curved piezoelectric element 512 may correspond generally to that of concave piezoelectric element 312 of transducer 260. The annular piezoelectric element 412 may be attached at its inner circumference to a lower end of the anchor portion 52*c* of the support structure 50*c*. The electrodes 17, 19 are applied to the opposed surfaces 512*a*, 512*b*.

The curvature of the bowl-shaped piezoelectric elements 212, 312, 412, and 512 visible in FIGS. 14A-15B is exaggerated for the sake of clarity. Careful design using simulation tools, as described below, may be used to determine the proper curvature to optimize the transducer design.

Figure 16:
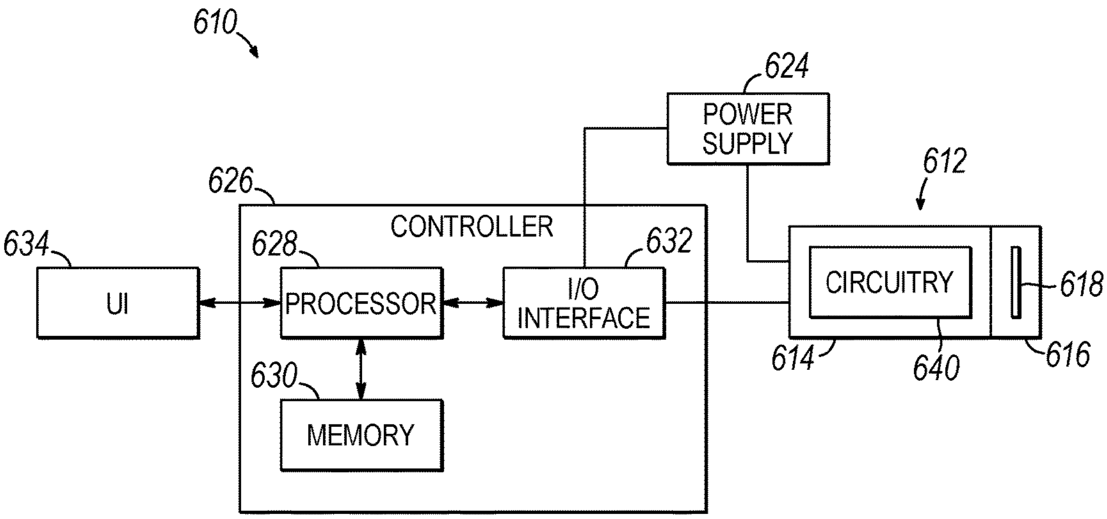
FIG. 16 is a diagrammatic view of a treatment and/or imaging system including a flextensional transducer in accordance with the embodiment of the invention.

With reference to FIG. 16, a treatment system 610 may include a treatment head 612 having a handpiece 614 and a cartridge 616 including a flextensional transducer 618, which may comprise any of the flextensional transducers described herein. Additionally, in one embodiment, the cartridge 616 may include a plurality of flextensional transducers, operating as an array. The treatment system 610 may further include a power supply 624 and a controller 626.

The controller 626 may include at least one processor 628, a memory 630, an input/output (I/O) interface 632, and a user interface 634 operatively coupled to the processor 628 of controller 626 in a known manner to allow a system operator to interact with the controller 626. The processor 628 may include one or more devices selected from microprocessors, micro-controllers, digital signal processors, microcomputers, central processing units, field programmable gate arrays, programmable logic devices, state machines, logic circuits, analog circuits, digital circuits, or any other devices that manipulate signals (analog or digital) based on operational instructions that are stored in the memory 630. Memory 630 may be a single memory device or a plurality of memory devices including but not limited to read-only memory (ROM), random access memory (RAM), volatile memory, non-volatile memory, static random access memory (SRAM), dynamic random access memory (DRAM), flash memory, cache memory, or any other device capable of storing digital information. Memory 630 may also include a mass storage device (not shown) such as a hard drive, optical drive, tape drive, non-volatile solid state device or any other device capable of storing digital information.

Processor 628 may operate under the control of an operating system that resides in memory 630. The operating system may manage controller resources so that instructions of computer program code embodied in one or more computer software applications residing in memory 630 may be executed by the processor 628. The processor 628 may execute the applications directly, in which case the operating system may be omitted.

The I/O interface 632 operatively couples the processor 628 to other components of the system 610, including the power supply 624 and circuitry 640 controlling the operation of the treatment head 612. The I/O interface 632 may include signal processing circuits that condition incoming and outgoing signals so that the signals are compatible with both the processor 628 and the components to which the processor 628 is coupled. To this end, the I/O interface 632 may include analog to digital (A/D) and/or digital to analog (D/A) converters, voltage level and/or frequency shifting circuits, optical isolation and/or driver circuits, and/or any other analog or digital circuitry suitable for coupling the processor 628 to the other components of the system 610.

The handpiece 616 and the flextensional transducer 618 may be operatively coupled by a cable to the power supply 624 and the controller 626. The power supply 624 may be configured to supply signals comprising an alternating-current voltage at a frequency that drives the flextensional transducer 618 at its resonant ultrasonic frequency. For example, the power supply 624 may supply an alternating current signal to the electrodes of the flextensional transducer 618 and thereby apply the electric field that drives the associated piezoelectric element 12 of the flextensional transducer 618 to vibrate so that the flextensional transducer 618 generates an acoustic signal. The power supply 624 may include a drive circuit configured to generate the alternating-current voltage to be inputted into the transducer 618 and a frequency controller configured to control a frequency of the alternating-current voltage. As described above, in one embodiment, the cartridge 616 may include a plurality of flextensional transducers 618 operating at similar or dissimilar resonant frequencies. In an embodiment where the cartridge 616 includes a plurality of transducers 618 operating at dissimilar resonant frequencies, the treatment system 610 may include a corresponding plurality of frequency controllers, each being assigned to a respective transducer 618 operating at a unique resonant frequency.

As described above, the performance characteristics of a flextensional transducer, such as its resonant frequencies, may be tuned by adjusting its physical configuration and the materials forming its components. Described below are a series of examples based on simulations performed using COMSOL Multiphysics® version 4.4, which is a software platform designed for modeling and simulating physics-based problems using finite element analysis. Also described below is simulation data demonstrating the relationship between transducer configuration (e.g., those configurations shown in the figures) and resonance frequency.

For Examples 1-44 described below, the following design parameters were held constant between all simulations: piezoelectric element thickness of 1 mm; endcap thickness of 0.25 mm; and endcap height of 0.5 mm (e.g., in FIG. 1, the axial distance between the plane defined by the surface 12*a* of the piezoelectric element 12 and the plane defined by the inner section 14*a* of the endcap 14 when the transducer 10 is not energized).

As used in the description of simulation data provided below, the term "maximum endcap displacement" refers to a maximum displacement of an endcap (e.g., at or near a inner section 14*a*, 16*a*, 80*a*, or 122*a* of endcaps 14, 16, 80, and 122, respectively) in an axial direction perpendicular to a plane defined by the piezoelectric element to which the endcap is attached.

In Examples 1-22 described below, each of the corresponding flextensional transducer configurations was modeled with a piezoelectric element having an outer diameter of 25.4 mm, or 1 inch.

In Example 1, a flextensional transducer having a construction similar to that of transducer 10 in FIG. 1 was modeled, and produced a maximum endcap displacement of 155 μm at a first resonance frequency of 10.3 kHz during simulation.

In Example 2, a flextensional transducer having a construction similar to that of transducer 100 in FIG. 3 was modeled, and produced a maximum endcap displacement of 223 μm at a first resonance frequency of 4.3 kHz during simulation.

In Example 3, a flextensional transducer having a construction similar to that of transducer 110 in FIG. 4 was modeled, and produced a maximum endcap displacement of 115 μm at a first resonance frequency of 9.7 kHz during simulation.

In Example 4, a flextensional transducer having a construction similar to that of transducer 120 in FIG. 5A was modeled, and produced a maximum endcap displacement of 21 μm at a first resonance frequency of 11.9 kHz during simulation.

In Example 5, a flextensional transducer having a construction similar to that of transducer 130 in FIG. 5B was modeled, and produced a maximum endcap displacement of 22.5 μm at a first resonance frequency of 9.1 kHz during simulation.

In Example 6, a flextensional transducer having a construction similar to that of transducer 140 in FIG. 5C was modeled, and produced a maximum endcap displacement of 59.2 μm at a first resonance frequency of 12.9 kHz during simulation.

In Example 7, a flextensional transducer having a construction similar to that of transducer 150 in FIG. 5D was modeled, and produced a maximum endcap displacement of 54.8 μm at a first resonance frequency of 12.9 kHz during simulation.

In Example 8, a flextensional transducer having a construction similar to that of transducer 160 in FIG. 6A was modeled, and produced a maximum endcap displacement of 22.2 μm at a first resonance frequency of 9.1 kHz during simulation.

In Example 9, a flextensional transducer having a construction similar to that of transducer 170 in FIG. 6B was modeled, and produced a maximum endcap displacement of 46.1 μm at a first resonance frequency of 12.2 kHz during simulation.

In Example 10, a flextensional transducer having a construction similar to that of transducer 180 in FIG. 7 with endcaps formed of acrylic was modeled, and produced a maximum endcap displacement of 125 μm at a first resonance frequency of 10.29 kHz during simulation.

In Example 11, a flextensional transducer having a construction similar to that of transducer 180 in FIG. 7 with endcaps formed of brass was modeled, and produced a maximum endcap displacement of 110 μm at a first resonance frequency of 10.4 kHz during simulation.

In Example 12, a flextensional transducer having a construction similar to that of transducer 190 in FIG. 8 with endcaps formed of acrylic was modeled, and produced a maximum endcap displacement of 126 μm at a first resonance frequency of 10.3 kHz during simulation.

In Example 13, a flextensional transducer having a construction similar to that of transducer 190 in FIG. 8 with endcaps formed of brass was modeled, and produced a maximum endcap displacement of 103 μm at a first resonance frequency of 10.8 kHz during simulation.

In Example 14, a flextensional transducer having a construction similar to that of transducer 200 in FIG. 9 was modeled, and produced a maximum endcap displacement of 80.3 μm at a first resonance frequency of 10.74 kHz during simulation.

In Example 15, a flextensional transducer having a construction similar to that of transducer 210 in FIG. 10 was modeled, and produced a maximum endcap displacement of 94.8 μm at a first resonance frequency of 5.74 kHz during simulation.

In Example 16, a flextensional transducer having a construction similar to that of transducer 220 in FIG. 11 was modeled, and produced a maximum endcap displacement of 94.8 μm at a first resonance frequency of 5.74 kHz during simulation.

In Example 17, a flextensional transducer having a construction similar to that of transducer 230 in FIG. 12 was modeled, and produced a maximum endcap displacement of 60.8 μm at a first resonance frequency of 5.41 kHz during simulation.

In Example 18, a flextensional transducer having a construction similar to that of transducer 240 in FIG. 13 was modeled, and produced a maximum endcap displacement of 85.3 μm at a first resonance frequency of 4.9 kHz during simulation.

In Example 19, a flextensional transducer having a construction similar to that of transducer 250 in FIG. 14A was modeled, and produced a maximum endcap displacement of 57.6 μm at a first resonance frequency of 5.4 kHz during simulation.

In Example 20, a flextensional transducer having a construction similar to that of transducer 260 in FIG. 14B was modeled, and produced a maximum endcap displacement of 88 μm at a first resonance frequency of 5.4 kHz during simulation.

In Example 21, a flextensional transducer having a construction similar to that of transducer 270 in FIG. 15A was modeled, and produced a maximum endcap displacement of 90 μm at a first resonance frequency of 4.1 kHz during simulation.

In Example 22, a flextensional transducer having a construction similar to that of transducer 280 in FIG. 15B was modeled, and produced a maximum endcap displacement of 78 μm at a first resonance frequency of 4 kHz during simulation.

In sample Examples 23-44 described below, each of the corresponding flextensional transducer configurations was modeled and simulated so as to yield a first resonance frequency of approximately 40 kHz±5%. Output data noted below for each transducer configuration includes a maximum endcap displacement and a piezoelectric element outer diameter corresponding to the respective transducer configuration at the stated first resonance frequency.

In Example 23, a flextensional transducer having a construction similar to that of transducer 10 in FIG. 1 was simulated at a first resonance frequency of 39.1 kHz, and produced a maximum endcap displacement of 41.3 μm with a piezoelectric element having an outer diameter of 12.7 mm.

In Example 24, a flextensional transducer having a construction similar to that of transducer 100 in FIG. 3 was simulated at a first resonance frequency of 39.8 kHz, and produced a maximum endcap displacement of 19.6 μm with a piezoelectric element having an outer diameter of 8.2 mm.

In Example 25, a flextensional transducer having a construction similar to that of transducer 110 in FIG. 4 was simulated at a first resonance frequency of 40.1 kHz, and produced a maximum endcap displacement of 58 μm with a piezoelectric element having an outer diameter of 5.9 mm.

In Example 26, a flextensional transducer having a construction similar to that of transducer 120 in FIG. 5A was simulated at a first resonance frequency of 42.8 kHz, and produced a maximum endcap displacement of 6.98 μm with a piezoelectric element having an outer diameter of 12.7 mm.

In Example 27, a flextensional transducer having a construction similar to that of transducer 130 in FIG. 5B was simulated at a first resonance frequency of 39.5 kHz, and produced a maximum endcap displacement of 10 μm with a piezoelectric element having an outer diameter of 13.8 mm.

In Example 28, a flextensional transducer having a construction similar to that of transducer 140 in FIG. 5C was simulated at a first resonance frequency of 39 kHz, and produced a maximum endcap displacement of 19.9 μm with a piezoelectric element having an outer diameter of 13.8 mm.

In Example 29, a flextensional transducer having a construction similar to that of transducer 150 in FIG. 5D was simulated at a first resonance frequency of 39 kHz, and produced a maximum endcap displacement of 19.4 μm with a piezoelectric element having an outer diameter of 13.8 mm.

In Example 30, a flextensional transducer having a construction similar to that of transducer 160 in FIG. 6A was simulated at a first resonance frequency of 38.5 kHz, and produced a maximum endcap displacement of 2.4 μm with a piezoelectric element having an outer diameter of 11.4 mm.

In Example 31, a flextensional transducer having a construction similar to that of transducer 170 in FIG. 6B was simulated at a first resonance frequency of 39 kHz, and produced a maximum endcap displacement of 15.3 μm with a piezoelectric element having an outer diameter of 13.8 mm.

In Example 32, a flextensional transducer having a construction similar to that of transducer 180 in FIG. 7 with acrylic endcaps was simulated at a first resonance frequency of 40.3 kHz, and produced a maximum endcap displacement of 64 μm with a piezoelectric element having an outer diameter of 17.8 mm.

In Example 33, a flextensional transducer having a construction similar to that of transducer 180 in FIG. 7 with brass endcaps was simulated at a first resonance frequency of 41.3 kHz, and produced a maximum endcap displacement of 52.4 μm with a piezoelectric element having an outer diameter of 17.8 mm.

In Example 34, a flextensional transducer having a construction similar to that of transducer 190 in FIG. 8 with acrylic endcaps was simulated at a first resonance frequency of 38.9 kHz, and produced a maximum endcap displacement of 34.6 μm with a piezoelectric element having an outer diameter of 12.7 mm.

In Example 35, a flextensional transducer having a construction similar to that of transducer 190 in FIG. 8 with brass endcaps was simulated at a first resonance frequency of 39.4 kHz, and produced a maximum endcap displacement of 28.3 μm with a piezoelectric element having an outer diameter of 12.7 mm.

In Example 36, a flextensional transducer having a construction similar to that of transducer 200 in FIG. 9 was simulated at a first resonance frequency of 41 kHz, and produced a maximum endcap displacement of 19 μm with a piezoelectric element having an outer diameter of 15 mm.

In Example 37, a flextensional transducer having a construction similar to that of transducer 210 in FIG. 10 was simulated at a first resonance frequency of 38 kHz, and produced a maximum endcap displacement of 4.4 μm with a piezoelectric element having an outer diameter of 10 mm.

In Example 38, a flextensional transducer having a construction similar to that of transducer 220 in FIG. 11 was simulated at a first resonance frequency of 40 kHz, and produced a maximum endcap displacement of 26.9 μm with a piezoelectric element having an outer diameter of 12.7 mm.

In Example 39, a flextensional transducer having a construction similar to that of transducer 230 in FIG. 12 was simulated at a first resonance frequency of 40 kHz, and produced a maximum endcap displacement of 14.9 μm with a piezoelectric element having an outer diameter of 11 mm.

In Example 40, a flextensional transducer having a construction similar to that of transducer 240 in FIG. 13 was simulated at a first resonance frequency of 40 kHz, and produced a maximum endcap displacement of 9.4 μm with a piezoelectric element having an outer diameter of 9 mm.

In Example 41, a flextensional transducer having a construction similar to that of transducer 250 in FIG. 14A was simulated at a first resonance frequency of 42 kHz, and produced a maximum endcap displacement of 17 μm with a piezoelectric element having an outer diameter of 13 mm.

In Example 42, a flextensional transducer having a construction similar to that of transducer 260 in FIG. 14B was simulated at a first resonance frequency of 39.7 kHz, and produced a maximum endcap displacement of 7 μm with a piezoelectric element having an outer diameter of 13 mm.

In Example 43, a flextensional transducer having a construction similar to that of transducer 270 in FIG. 15A was simulated at a first resonance frequency of 40.9 kHz, and produced a maximum endcap displacement of 9 μm with a piezoelectric element having an outer diameter of 8 mm.

In Example 44, a flextensional transducer having a construction similar to that of transducer 280 in FIG. 15B was simulated at a first resonance frequency of 38.6 kHz, and produced a maximum endcap displacement of 7 μm with a piezoelectric element having an outer diameter of 9 mm.

With the benefit of software simulation data such as that produced by Examples 1-44, described above, persons of ordinary skill in the art may design a flextensional transducer having a construction similar to that of any one of, or a combination of, the embodiments shown and described herein, and having performance characteristics that are optimal for a desired application.

For example, for an application where a flextensional transducer having a piezoelectric element with an outer diameter of 25.4 mm is preferred, and where the application requires maximum possible endcap deflection, the data of Examples 1-22 may be interpreted to indicate that the configuration of transducer 100 shown in FIG. 3 may be an optimal design selection (see Example 2).

As another example, for an application where a flextensional transducer having a piezoelectric element with an outer diameter of 25.4 mm is preferred, and where the application requires maximum possible endcap deflection and a transducer having a compact configuration, the data of Examples 1-22 may be interpreted to indicate that the configuration of transducer 190 shown in FIG. 8, with endcaps formed of acrylic, may be an optimal design selection (see Example 12).

In another example, for an application where a flextensional transducer having a first resonance frequency of approximately 40 kHz is preferred, and where the application requires maximum possible endcap deflection, the data of Examples 23-44 may be interpreted to indicate that the configuration of transducer 180 shown in FIG. 7, with endcaps formed of acrylic, may be an optimal design selection (see Example 32).

In another example, for an application where a flextensional transducer having a first resonance frequency of approximately 40 kHz is preferred, and where the application requires maximum possible endcap deflection and a transducer having a compact configuration, the data of Examples 23-44 may be interpreted to indicate that the configuration of transducer 190 shown in FIG. 8, with endcaps formed of acrylic, may be an optimal design selection (see Example 34).

The data of Examples 1-44 described above may be interpreted in various additional ways by persons having ordinary skill in the art for purposes of designing a flextensional transducer having optimal performance characteristics for a desired application.

It will be understood that when an element is described herein as being "connected," "coupled," or "attached" to or with another element, it can be directly connected, coupled, or attached to the other element or, instead, one or more intervening elements may be present. In contrast, when an element is described as being "directly connected," "directly coupled," or "directly attached" to or with another element, there are no intervening elements present. When an element is described as being "indirectly connected," "indirectly coupled," or "indirectly attached" to or with another element, there is at least one intervening element present.

While the present invention has been illustrated by the description of specific embodiments thereof, and while the embodiments have been described in considerable detail, it is not intended to restrict or in any way limit the scope of the appended claims to such detail. The various features discussed herein may be used alone or in any combination. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of the general inventive concept.

What is claimed is:

1. A flextensional transducer comprising:

a piezoelectric element; and an endcap having a first portion attached to the piezoelectric element and a second portion in a non-contacting relationship with the piezoelectric element, wherein the first portion of the endcap is annular and radially surrounds the second portion of the endcap, the first portion of the endcap is comprised of a metal, and the second portion of the endcap is comprised of a material having a lower stiffness than the metal of the first portion of the endcap.

2. The flextensional transducer of claim 1 wherein the material comprising the second portion of the endcap has a greater flexibility than the metal comprising the first portion of the endcap.

3. The flextensional transducer of claim 1 wherein the material comprising the second portion of the endcap includes a polymer.

4. The flextensional transducer of claim 1 wherein the piezoelectric element is annular and the material comprising the second portion of the endcap is configured to permit light to pass through the endcap.

5. The flextensional transducer of claim 1 wherein the endcap is directly attached to the piezoelectric element.

6. The flextensional transducer of claim 1 comprising:

a ring structure positioned in abutting contact with an outer circumference of the piezoelectric element, wherein the endcap is attached directly to the ring structure, and the ring structure is configured to radially expand with the piezoelectric element and to transfer mechanical energy from the piezoelectric element to the endcap.

7. A method of emitting sound energy with a flextensional transducer, the method comprising:

energizing a piezoelectric element with an alternating current signal so that the piezoelectric element generates mechanical energy;

transferring the mechanical energy from the piezoelectric element to an endcap having a first portion attached to the piezoelectric element;

in response to the mechanical energy transfer, allowing a second portion of the endcap in a non-contacting relationship with the piezoelectric element to flex with a greater displacement in an axial direction than the first portion of the endcap; and emitting the sound energy from the at least one endcap as a result of the flexing of the endcap, wherein the first portion of the endcap is annular and radially surrounds the second portion of the endcap, the first portion of the endcap is comprised of a metal, and the second portion of the endcap is comprised of a material having a lower stiffness than the metal of the first portion of the endcap.

8. The method of claim 7 wherein transferring the mechanical energy from the piezoelectric element to the endcap comprises:

transferring the mechanical energy from the piezoelectric element to a ring structure; and transferring the mechanical energy from the ring structure to the endcap.

9. The flextensional transducer of claim 1 wherein the second portion of the endcap has a planar surface, and the piezoelectric element has a planar surface that is parallel to the planar surface of the second portion of the endcap.

10. The flextensional transducer of claim 9 wherein the endcap is oriented to be generally concave with respect to the planar surface of the piezoelectric element.

11. The flextensional transducer of claim 1 wherein the material comprising the second portion of the endcap is a non-metal.

12. The flextensional transducer of claim 1 wherein the first portion of the endcap has a chamfered surface, and the second portion of the endcap has a chamfered surface that is configured to mate and bond with the chamfered surface of the first portion.

13. The flextensional transducer of claim 1 wherein the metal comprising the first portion of the endcap is brass, aluminum, or stainless steel, and the material comprising the second portion of the endcap is polyurethane or polycarbonate.

14. The flextensional transducer of claim 4 wherein the piezoelectric element is configured to generate sound energy, and the end cap is configured to emit the sound energy generated by the piezoelectric element from the flextensional transducer to simultaneously or sequentially expose tissue to stimulation by the light and the sound energy.

15. The flextensional transducer of claim 4 wherein the piezoelectric element is configured to generate sound energy, and the end cap is configured to emit the sound energy generated by the piezoelectric element from the flextensional transducer to simultaneously or sequentially expose a biofilm to stimulation by the light and the sound energy.

16. The flextensional transducer of claim 4 wherein the piezoelectric element includes an aperture that provides an optical path for the light through the piezoelectric element.

17. The flextensional transducer of claim 4 wherein the second material is transparent or translucent.

18. The method of claim 7 further comprising:

generating light with a light source;

transmitting the light through the second portion of the endcap; and simultaneously or sequentially exposing tissue to stimulation by the light and the sound energy.

19. The method of claim 18 further comprising:

directing the light through an aperture in the piezoelectric element that provides an optical path for the light through the piezoelectric element.

20. The method of claim 18 wherein the material of the second portion is transparent or translucent.

21. The method of claim 7 further comprising:

generating light with a light source;

transmitting the light through the second portion of the endcap; and simultaneously or sequentially exposing a biofilm to stimulation by the light and the sound energy.

22. The method of claim 21 further comprising:

directing the light through an aperture in the piezoelectric element that provides an optical path for the light through the piezoelectric element.

23. The method of claim 21 wherein the material of the second portion is transparent or translucent.

24. The method of claim 7 wherein the first portion of the endcap has a chamfered surface, and the second portion of the endcap has a chamfered surface that is configured to mate and bond with the chamfered surface of the first portion.

25. The method of claim 7 wherein the metal comprising the first portion of the endcap is brass, aluminum, or stainless steel, and the material comprising the second portion of the endcap is polyurethane or polycarbonate.

* * * * *